United States Patent [19]

Dumaitre et al.

[11] 4,432,984
[45] Feb. 21, 1984

[54] ANTI-HYPERTENSIVE BENZODIOXAN DERIVATIVES

[75] Inventors: Bernard Dumaitre, Bobigny; Claude Perrin, Orsay; Pierre-Jean Cornu, Paris; Gilles Streichenberger, Neuilly-sur-Seine, all of France

[73] Assignee: Emile Bouchara, Paris, France

[21] Appl. No.: 269,411

[22] Filed: Jun. 1, 1981

Related U.S. Application Data

[63] Continuation of Ser. No. 134,476, Mar. 27, 1980, abandoned, which is a continuation-in-part of Ser. No. 11,162, Feb. 9, 1979, abandoned.

[51] Int. Cl.³ .................. A61K 31/445; C07D 405/06
[52] U.S. Cl. .................................. 424/267; 546/197; 546/225; 546/236
[58] Field of Search ......................... 546/197; 424/267

[56] References Cited

U.S. PATENT DOCUMENTS 4,101,663  7/1978  Helsley et al. .................. 546/201 X

FOREIGN PATENT DOCUMENTS 1404003  8/1975  United Kingdom ................ 546/201

OTHER PUBLICATIONS

Loewenthal, E., in *Protective Groups in Organic Chemistry* (McOmie, Editor), Plenum Press, N.Y., 1973, pp. 327–328.

*Primary Examiner*—Richard A. Schwartz
*Attorney, Agent, or Firm*—Young & Thompson

[57] ABSTRACT

This invention relates to benzodioxanylalkylpiperidines, to processes for producing them and to the pharmaceutical compositions containing such compounds as active ingredient.

This invention also relates to a method for treating hypertension in hypertensive mammals.

5 Claims, No Drawings

ANTI-HYPERTENSIVE BENZODIOXAN DERIVATIVES

This application is a continuation of my application Ser. No. 139,476, filed Mar. 27, 1980, now abandoned, which in turn was a continuation-in-part of my then copending application Ser. No. 11,162 filed Feb. 9, 1979 and now abandoned.

PRIOR ART

The prior art may be illustrated with:
J. L. ARCHIBALD, J Med Chem 1974, 17, 736
J. L. ARCHIBALD and cowork, J Med Chem 1971, 14, 1054.

SUMMARY OF THE INVENTION

This invention relates to benzodioxanylalkylpiperidine, the para position of this nitrogen-containing ring being substituted with an aroyl radical. They are represented with the formula I

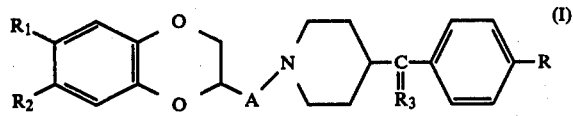

in which $R_1$ and $R_2$ the same or different are a hydrogen or a substituent selected from the group consisting of lower alkyl, lower alkoxy and halogen.

R is an hydrogen, a halogen, lower alkyl, a hydroxy, a lower alkoxy, a lower alkylcarbonyloxy, radical.

A is a lower alkyl chain of 1 to 3 carbon atoms which may be substituted.

$R_3$ is an oxygen or the

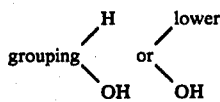

These compounds may be solified by adding a mineral or organic acid, preferably a therapeutically compatible mineral or organic acid.

These compounds may further be resolved into their optically active forms.

They are utilized in the form of pharmaceutical compositions containing at least one of these compounds or a salt thereof in addition or admixture with an inert non-toxic therapeutically-compatible carrier or vehicle.

They are valuable medicines for treating hypertension in mammals.

PREFERRED EMBODIMENTS

This invention relates to novel benzodioxan derivatives, to processes for producing them and to pharmaceutical compositions containing them.

The novel benzodioxan derivatives according to this invention have the following formula I

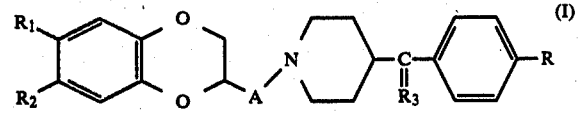

in which $R_1$ and $R_2$, the same or different, are a hydrogen atom or a substituent selected from the group consisting of a lower alkyl radical, a lower alkoxy, a halogen and a hydroxy.

R is a hydrogen atom or a substituent selected from the group consisting of a halogen, a lower alkyl radical, a hydroxy, a lower alkoxy and a lower (alkyl carbonyl) oxy radical.

A is a lower alkylene linkage having from 1 to 3 carbon atoms which may be substituted with a hydroxy radical.

$R_3$ is an oxygen or the

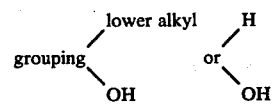

The compounds of formula I may be salified by adding a mineral or organic acid. The therapeutically-compatible mineral or organic acids are the preferred ones. However addition salts with other acids may also be of value as a mean for resolving, isolating or purifying the compounds of formula I.

Examples of salts with acids are the hydrochloride, the hydrobromide, the nitrate, the sulfates, the sulfites, the phosphates, the formates, the acetates, the benzoate, the 2,4-dichloro benzoate, the 3, 4, 5-trimethoxy benzoate, the vanillate, the O-carbethoxy syringoate, the naphtoates, the benzenesulfonate, the methanesulfonate, the isethionate, the nicotinate, the embonate, and the glucose phosphates.

As a mean for resolving the compounds of formula I, an optically-active acid may be used such as d-tartaric acid, ditoluyl d-tartaric acid, NN-diethyl d-tartramic acid or 4-hydroxy proline.

Generally speaking a lower alkyl radical is a hydrocarbyl chain having from 1 to 6 carbon atoms such as the methyl, ethyl, isopropyl, sec butyl, tert butyl, pentyl, neo pentyl and h-hexyl radicals.

The lower alkoxy radicals have from 1 to 6 carbon atoms in the alkyl chain which may be a straight or branched chain such as methoxy, ethoxy, isopropoxy, tertbutoxy or pentyloxy radicals.

The lower alkylcarbonyloxy is a hydroxy substituted with a hydrocarbyl carbonyl chain in which the hydrocarbyl moiety has from 1 to 5 carbon atoms, in a straight or branched chain.

As far as this invention is concerned the linkage A is an alkylene radical of 1 to 3 carbon atoms. It may be defined as a group having the formula II $$-D-E- \quad (II)$$

wherein D is a methylene or a hydroxy methylene and E is a direct carbon-carbon bond, a methylene or an ethylene radical.

Accordingly, A may be defined as a methylene, an ethylene, a propylene or a hydroxyethyl radical.

The length of this linkage is of some importance for the pharmacological properties of the compounds of formula I and the intensity or duration of their activity may be modulated by altering the number of carbon atoms of this moiety.

As presently preferred compounds, they may be cited
1-[(2,3-dihydro [4H] 1,4-benzodioxin)-2-yl] methyl 4-(4-fluoro benzoyl) piperidine and its hydrochloride
1-[(2,3-dihydro [4H] 1,4-benzodioxin)-2-yl)] methyl 4-(4-methoxy benzoyl) piperidine and its fumarate 1-[(2,3-dihydro [4H] 1,4-benzodioxin)-2-yl] methyl 4-benzoyl piperidine and its hydrochloride 1-[(2,3-dihydro [4H] 1,4-benzodioxin)-2-yl)] methyl 4-(4-fluoroα-methylα-hydroxy benzyl) piperidine and its hydrochloride.

1-[(2,3-dihydro [4H] 1,4-benzodioxin)-2-yl] methyl 4-(4-fluoroα-hydroxy benzyl) piperidine and its hydrochloride.

This invention also provides a process for producing a compound of formula I in which A is a hydrocarbyl chain which comprises the steps of reacting a 4-benzoyl piperidine of the formula III

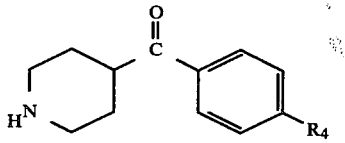

in which R₄ is a hydrogen atom, a lower alkyl, a lower alkoxy, a hydroxy or a halogen,
with a carbonyl blocking agent to produce a protected benzoyl piperidine of the formula IV

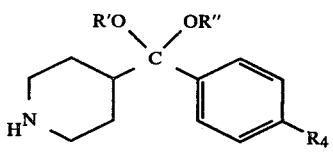

in which R' and R" are a lower alkyl or a lower alkylene radical having from 2 to 3 carbon atoms.
and R₄ is defined as above-given
contacting the latter with a (benzodioxanyl alkyl) ester of the formula V

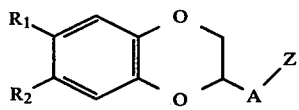

in which R₁ and R₂ have the above-given definitions.
A is a lower alkylene chain and
Z is the residue of an ester function which may be easily split
producing a benzodioxanyl derivative of formula VI

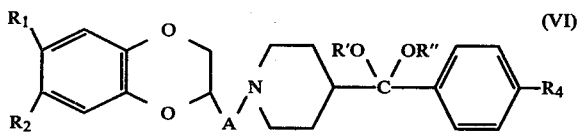

wherein R₁ and R₂ have the above given definition
R' and R" are a lower alkyl or a lower alkylene radical having from 2 to 3 carbon atoms
R₄ has the above given definitions and A is a lower alkylene chain
which is converted into a compound of formula I

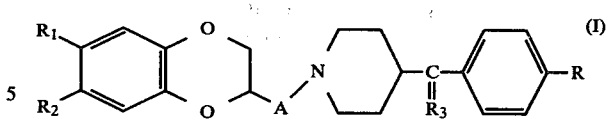

wherein R₃ is an oxygen and R₁, R₂, R₃ and A have the previously given definitions by acid hydrolysis or functional exchange.

The compounds of formula I may be further acylated when R₄ is a hydroxy to produce a compound of formula I wherein R₄ is a lower alkylcarbonyloxy radical or salified by adding a mineral or organic acid or resolved into their optically-active isomers by adding an optically-active organic acid or reduced by means of a reducing or alkylating agent.

As a preferred mean for producing a compound of formula I the carbonyl-blocking agent will be a lower alkanol or a polyol to produce the corresponding ketal or cyclic ketal such as a dioxolan. Example of such a blocking-agent will be ethylene glycol in the presence of an acid such as p-toluenesulphonic acid.

The reactive ester of formula V will be preferably a halide, a lower alkyl sulfonyl ester such as the methyl sulfonyl ester or the p-toluenesulfonylester.

The regeneration of the ketone function is performed using an acid such as hydrochloric acid or perchloric acid or a functional exchange with a carbonylcarboxylic acid such as glyoxylic acid, pyruvic acid or 1-ketogulonic acid.

The reaction between the reactive ester V and the piperidine of formula III is performed in an inert solvent such as a high-boiling hydrocarbon solvent for example toluene or xylene or a polar aprotic solvent such as dimethyl formamide or dimethyl acetamide. Preferably this condensation is achieved in the presence of a proton binding agent such as an alkali metal carbonate or an earth alkali metal carbonate.

The starting material have been obtained according to known methods. The compounds of formula III for which R₄ is a hydroxy are obtained from the corresponding methoxy derivative by demethylating it using hydrobromic acid. The reactive esters of formula V are produced from the 2-hydroxyalkyl 2,3-dihydro [4H] benzodioxin by reaction with a hydrohalic acid or with a reactive derivative of a lower alkyl sulphonic acid or of a phenyl sulphonic acid, such as methone sulphonyl chloride or p-toluenesulphonyl chloride.

The 2-hydroalkyl 2,3-dihydro [4H] benzodioxins are obtained from pyrocatechol or a substituted 1,2-dihydroxy benzene with the suitable halohydrin, preferably a chloroalkylene oxyde such as epichlorhydrin.

The 4-benzoyl piperidines of formula III are conveniently prepared by reacting a N-acetyl isonipecotic acid chloride as the hydrochloride with the requested phenyl derivative in the Friedel-Craft reaction conditions. The resulting carbonylated derivative is further deacylated by heating it in hydrochloric medium.

The piperidines of formula III may also be prepared in reacting a 4-pyridine carboxylic acid chloride, as the hydrochloride, with the required phenyl derivative and the resulting pyridylcarbonylphenyl derivative is thereafter hydrogenated in the presence of a Catalyst to produce the suitable piperidine of formula III.

The compounds of formula V wherein A is a lower alkylene having more than one carbon may be obtained from a hydroxymethylated of formula VII

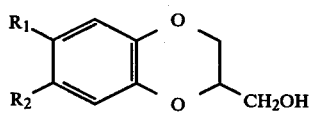 (VII)

wherein $R_1$ and $R_2$ are defined as previously given converting it into a halogenomethylated derivative of formula VIII

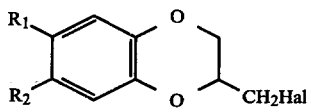 (VIII)

wherein $R_1$ and $R_2$ are defined as above given and Hal is a halogen atom having a molecular weight higher than 19
by means of a halogenating agent, reacting the latter with an alkali metal cyanide to produce a cyanomethylated derivative of the formula IX

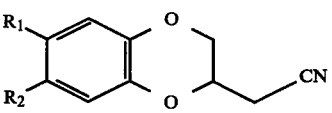 (IX)

which is hydrolysed in acidic medium to produce a substituted acetic acid, esterifies the latter with a lower alkanol to produce the lower alkyl ester thereof which is further reduced by means of an alkali metal mixed hydride to produce the hydroxy ethylated derivative of formula X

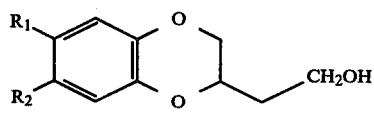 (X)

which is converted into a reactive ester of formula XI

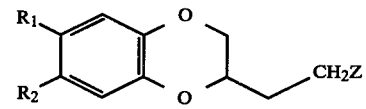 (XI)

in which $R_1$, $R_2$ and Z have the above-given definitions.

The compounds of formula XI may be condensed either with the substituted piperidine of formula IV to produce a benzodioxanyl derivative of formula VI or with an alkali metal cyanide to produce a compound of formula VIII having one more carbon atom.

The compounds of formula V

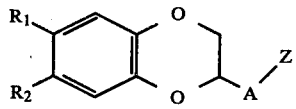 (V)

in which Z, $R_1$ and $R_2$ have the above-given definition and A is a hydroxy lower alkylene radical may be conveniently produced from a benzodioxanyl derivative of the formula

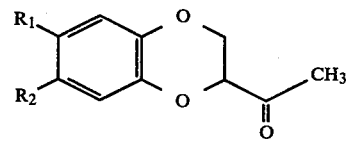

wherein $R_1$ and $R_2$ have the above-given definitions. halogenating the latter by means of a halogenating agent to produce a compound of formula

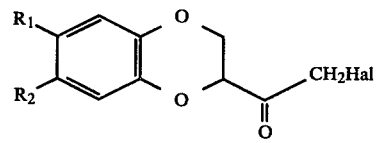

in which $R_1$ and $R_2$ have the above-given definitions and Hal is a bromine, chlorine or iodine atom. reducing this α-halogenated ketone into the αhalohydrin of the formula

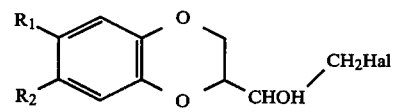

reacting it either with a substituted piperidine of formula IV to produce a compound of formula VI or with an alkali metal cyanide to produce the cyanoethylated derivative. The latter is further hydrolysed to the corresponding β-hydroxy propionic acid, esterifying the latter into a lower alkyl ester then reducing to the corresponding propane 1,3-diol, contacting it with methane sulphonyl choride to produce the corresponding 3-hydroxy 1-methane sulphonyloxy propane, and reacting the latter with a substituted piperidine of formula IV.

In order to produce a compound of formula I wherein $R_3$ is a hydroxy group, the corresponding carbonylated derivative of formula I is reduced by means of an alkali metal hydride, an alkali metal mixed hydride or aluminium isopropylate.

In order to produce a compound of formula I wherein $R_3$ is the

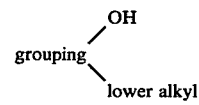

the corresponding carbonylated derivative of formula I (wherein $R_3$ is an oxygen) is reacted with a alkyl metal halide and the corresponding alkyl carbinol is recovered. Preferably the alkyl metal halide is an alkyl magnesium halide, an alkyl cadmium halide, an alkyl copper halide or an alkyl zinc halide.

The compounds of formula V wherein $R_1$ and/or $R_2$ are substituents selected from the group consisting of hydroxy, lower alkoxy and halogen are conveniently obtained from the unsubstituted benzodioxan by nitration, reduction of the resulting nitro derivative into an amino derivative, diazotation of this arylamine and decomposition of the diazonium salt in the presence of a copper salt.

The compounds of formula I and their salts have interesting pharmacological properties. They exert in the hypertensive mammals a very potent antihypertensive activity.

These compounds appear to be antagonized with a sympatholytic compound having a central activity such as yohimbine or piperoxan. The pharmacological action of the compounds of formula I may thus be considered as a sympathomimetic agent like clonidine and more precisely a presynaptica-sympathomimetic agent. This mechanism of action is quite different of that of some related chemical compounds such as indoramin which is a α-blocking agent.

The compounds of formula I and the acid addition salts thereof are utilized as active ingredients of pharmaceutical compositions. According to this invention this is a subject to provide pharmaceutical compositions containing as active ingredient at least one compound of formula I or a salt thereof in addition or in conjunction with an inert non-toxic pharmaceutical carrier or vehicle.

Among the intended pharmaceutical compositions, it may particularly be cited those intended for the parenteral way of administration, for the oral way, the sublingual way, the rectal way and the permucous way. They may be the tablets, the coated tablets, the dragees, the soft gelatine capsules, the drops, the syrups, the drinkable solutions or suspensions, the ampoules, the phials, the multidosis flasks, the autoinjectable syringes, the sublingual tablets, the suppositories or the solutions in a polar solvent for percutaneous administration.

The usual dosology may broadly vary depending on the age, the weight of the patient, the disease to be treated and the way of administration. As a general rule, the usual dosology in the men will range from 10 to 200 mg per unit dosage and from 20 to 400 mg daily. The preferred dosage ranges from 30 to 80 mg daily.

This invention also provides a method for treating hypertension in hypertensive mammals which comprises administering to said patients a safe but effective amount of a compound of formula I or a salt thereof.

In a preferred manner the safe but effective amount of a compound of formula I will range from 10 to 100 mg daily. This amount will be converted when an acid addition salt is used, on a weight basis. Similarly in the veterinary medecine the amount to be daily administered will range from 0.30 mg/kg to 6.66 mg/kg.

The following examples are merely intended to illustrate the invention. They do not limit it in any manner. The temperatures are expressed in degrees Centigrade.

EXAMPLE I

4-[(4-fluoroα-ethylenedioxy) benzyl] piperidine

Step A N-acetyl isonipecotic acid chloride 1000 g isonipecotic acid are suspended in 4000 g acetic anhydride and heated to reflux for 2 hours. The mixture is thereafter evaporated to dryness under reduced pressure. The crystalline residue is taken up in 6000 ml ether. The residue is separated by succion-filtration, washed with ether and dried. 965 g N-acetyl isonipecotic acid are recovered, melting at 180°–182°.

This compound is converted into its chloride by dissolving 1063 g N-acetyl isonipecotic acid into 6000 g thionyl chloride at room temperature and letting the mixture aside for 24 hours. The mixture is then diluted with n-hexane. The chloride precipitates and is recovered. 1300 g of the acid chloride is obtained. Its melting point is 120°.

Step B 4-(4-fluorobenzoyl) piperidine

A mixture of 3000 g of fluorobenzene and 1680 g aluminium chloride is kept under stirring while 1300 g N-acetyl isonipecotic acid chloride is portionwise added. Once this addition is achieved the whole mixture is heated to reflux then let to revert to room temperature.

The reagent in excess is destroyed with water and the aqueous suspension is extracted with ethyl acetate. 1475 g of row 4-(fluoro benzoyl)N-acetyl piperidine is thus obtained as an oily residue.

The (4-fluorobenzoyl) N-acetyl piperidine is thereafter hydrolysed with 1050 g hydrochloric acid and 1300 ml water. The solvent is evaporated off and taken up with isopropanol.

1064 g 4-(4-fluorobenzoyl) piperidine are recovered as the hydrochloride.

The free base is produced by suspending the hydrochloride in 4500 g methanol and adding to the suspension 1635 g of a 2.75 N solution of sodium hydroxide in ethanol.

The sodium chloride which precipitates is separated. The ethanolic solution is evaporated to dryness at ambient temperature. 1019 g 4-(4-fluorobenzoyl) piperidine are thus obtained. It is further purified by dissolving it in benzene. The benzenic solution is concentrated until the crystallisation initiates. After 12 hours of contact, 920 g of 4-(4-fluorobenzoyl) piperidine are obtained after filtration and drying.

Step C

4-[(4-Fluoro-α-ethylenedioxy)benzyl]-piperidine

In a reactor provided with a Dean-Stark water-trap are added 22 parts 4-(4-fluorobenzoyl)piperidine, 21 parts p-toluenesulfonic acid, 50 parts ethylene glycol and 250 parts benzene, after which the reaction mixture is heated to the boiling temperature for 16 hours, with stirring, while removing the water by azeotropy. After cooling to 0° C., 2 N sodium hydroxide (65 parts) is added and the organic phase is decanted off. The latter is washed with water, dried and concentrated under reduced pressure, to give 21 parts of a white solid. M.p.: 70° C.

The compound is sufficiently pure to be used in the subsequent steps of the synthesis.

Step D

1-[(2,3-Dihydro-4H-1,4-benzodioxin)-2-ylmethyl]-4-[(4-fluoro-α-ethylenedioxy)benzyl]piperidine hydrochloride A mixture of 27 parts 2-hydroxymethyl-2,3-dihydro-4H-1,4-benzodioxine methanesulfonate, 25 parts 4-[(4-fluoro-α-ethylenedioxy)benzyl]piperidine, 15 parts potassium carbonate and 200 parts toluene are heated to the boiling temperature for 18 hours, with stirring. After cooling, the material is filtered and the filtrate is made acidic, with vigorous stirring, with 50 parts 20% HCl.

The resulting crystals are suction filtered and washed with ether, to give 26 parts of product, M.P.: 220° C.

Step E

1-[(2,3-dihydro-4H-1,4-benzodioxin)-2-ylmethyl]-4-(4-fluorobenzoyl)piperidine A mixture of 100 parts 1-[(2,3-dihydro-4H-1,4-benzodioxin)-2-ylmethyl]-4-[(4-fluoro-α-ethylenedioxy)-benzyl]-piperidine hydrochloride, 200 parts concentrated HCl, 400 parts isopropanol and 100 parts water is heated to the boiling temperature for 2.5 hours. It is then concentrated to dryness, treated with water, made slightly basic with NaOH, extracted with ethyl acetate, after which the organic phase is separated.

Washing with water, drying and concentration to dryness produce 74 parts of a white solid, M.p.: 95°–96° C.

EXAMPLE 2

1-[(2,3-Dihydro-4H-1,4-benzodioxin)-2-ylmethyl]-4-(4-fluorobenzoyl)piperidine hydrochloride 50 Parts 1-[(2,3-dihydro-4H-1,4-benzodioxin)-2-ylmethyl]-4-(4-fluorobenzoyl)piperidine are dissolved in 1000 parts ether and the stoichiometric amount of hydrochloric acid solution in anhydrous ether is then added thereto, and the hydrochloride precipitates out.

Filtration and washing with ether give 52 parts of product which may be purified by recrystallization from isopropyl alcohol, to give white scales, M.p.=195°–196° C.

EXAMPLE 3

1-[(2,3-Dihydro-4H-1,4-benzodioxin)-2-ylmethyl]-4-(4-methoxy-benzoyl)piperidine A mixture of 24 parts 2-hydroxymethyl-2,3-dihydro-4H-1,4-benzodioxine methanesulfonate, 22 parts 4-methoxybenzoylpiperidine, 14 parts potassium carbonate in 200 parts anhydrous xylene is heated to the boiling temperature for 16 hours.

After cooling, the material is washed with water and treated with normal hydrochloric acid in heterogeneous phase, which precipitates the desired product as an oil.

The oil is separated, the free base is released with dilute sodium hydroxide and is extracted with ethyl acetate, to give, after washing with water, drying and concentration, 25 parts of product which remains in the form of an oil.

EXAMPLE 4

1-[(2,3-Dihydro-4H-1,4-benzodioxin)-2-ylmethyl]-4-(4-methoxybenzoyl)piperidine fumarate 25 Parts 1-[-2,3-dihydro-4H-1,4-benzodioxin)-2-ylmethyl]-4-(4-methoxybenzoyl)piperidine are dissolved in 100 parts ethanol and 8 parts fumaric acid dissolved in 100 parts ethanol are added thereto.

The resulting material is filtered and allowed to crystallize, which gives 19 parts fumarate which may be purified by recrystallization from ethanol. White crystals. M.p.=170° C.

EXAMPLE 5

1-[(2,3-Dihydro-4H-1,4-benzodioxin)-2-ylmethyl]-4-(4-chloro-benzoyl)piperidine A mixture of 12.5 parts 2-hydroxymethyl-2,3-dihydro-4H-benzodioxine methanesulfonate, 10.5 parts 4-chlorobenzoylpiperidine and 7 parts potassium carbonate in 200 parts anhydrous xylene is heated for 16 hours to the boiling temperature.

After cooling, the resulting material is washed with water and treated with normal hydrochloric acid in heterogeneous phase.

After precipitation, the resulting oil is separated and the free base is released by treatment with dilute sodium hydroxide.

Extraction with ethyl acetate, washing with water and concentration give a solid which is recrystallized from isopropyl ether and treated with -black, to give 5 parts crystalline material, M.p.=120° C.

EXAMPLE 6

1-[(2,3-Dihydro-4H-1,4-benzodioxin)-2-ylmethyl]-4-(4-chlorobenzoyl)piperidine hydrochloride 5 Parts 1-[(2,3-dihydro-4H-1,4-benzodioxin)-2-ylmethyl]-4-(4-chlorobenzoyl)piperidine are dissolved in 50 parts hot ethanol, and the stoichiometric of ethereal hydrochloric acid solution is added thereto.

The product crystallizes on cooling, and subsequent separation gives 4.3 parts of white crystals, M.p.=223° C.

EXAMPLE 7

1-[(2,3-Dihydro-4H-1,4-benzodioxin)-2-ylmethyl]-4-(4-hydroxy-benzoyl)piperidine 32 Parts 1-[(2,3-dihydro-4H-1,4-benzodioxin)-2-ylmethyl]-4-(4-methoxy-benzoyl)piperidine are heated to the boiling temperature for 2 hours, with 400 parts 48% hydrobromic acid.

After cooling, the resulting material is poured into ice-water and the solid precipitate is separated and washed with water. It is then dissolved in methanol, in the hot, and made basic with NH4OH.

The resulting solution is concentrated to dryness and extracted with ethyl acetate. The material is then washed, dried and concentrated, to give a solid which is recrystallized from methanol. 22.5 parts white crystals are thus recovered. M.p.=94.5° C.

EXAMPLE 8

1-[(2,3-Dihydro-4H-1,4-benzodioxin)-2-ylmethyl]-4-(4-hydroxybenzoyl)piperidine nicotinate 3.5 Parts 1-[(2,3-dihydro-4H-1,4-benzodioxin)-2-ylmethyl]-4-(4-hydroxybenzoyl)piperidine are dissolved in 35 parts benzene and 20 parts pyridine.

4 Parts nicotinoyl chloride hydrochloride are then added portionwise thereto, with stirring, after which the reaction mixture is gently boiled for 16 hours.

The resulting material is poured over water, extracted with ethyl acetate; the organic phase is washed with dilute sodium hydroxide and then with water, and is then concentrated, to give 5 parts white crystals which may be purified by recrystallization from ethanol, M.p. 125° C.

EXAMPLE 9

1-[(2,3-Dihydro-4H-1,4-benzodioxin)-2-ylmethyl]-4-4-benzoyl-piperidine hydrochloride A mixture of 23.5 parts 4-[α-ethylene-dioxybenzyl]-piperidine, 24.5 parts 2-hydroxymethyl-2,3-dihydro-4H-1,4-benzodioxine methanesulfonate, 14 parts potassium carbonate and 300 ml toluene is refluxed for 18 hours in a reactor provided with a stirring device.

After cooling, the material is filtered and 100 parts of 20% HCl solution are added to the filtrate, with stirring.

The resulting crystals are filtered off and washed with ether, to give 29.5 parts 1-[(2,3-dihydro-4H-1,4-benzodioxin)-2-ylmethyl]-4-(α-ethylenedioxybenzyl)-piperidine. M.p.=235° C.

29.5 Parts of this compound are then boiled with 110 parts isopropanol, 30 parts H$_2$O and 30 parts concentrated HCl. After evaporation to dryness, the material is treated with water, neutralized with dilute NaOH and extracted with ethyl acetate, to give white crystals which are recrystallized from isopropyl ether, to produce 21 parts 1-[(2,3-dihydro-4H-1,4-benzodioxin)-2-ylmethyl]-4-benzoyl piperidine, M.p.=141° C.

The latter compound is converted to the hydrochloride by reaction with HCl within isopropanol. White crystals. M.p.=190°-192° C.

EXAMPLE 10

1-[(2,3-Dihydro-4H-1,4-benzodioxin)-2-ylmethyl]-4-(4-methylbenzoyl)piperidine hydrochloride.

A mixture of 25 parts 4-(4-methyl-α-ethylene-dioxybenzyl)piperidine, 24.5 parts 2-hydroxymethyl-2,3-dihydro-4H-1,4-benzodioxine methanesulfonate, 14 parts potassium carbonate and 300 parts dimethylformamide is heated to 100° C. for 24 hours in a reactor provided with a stirring device.

After cooling, the DMF is removed under reduced pressure and the resulting material is taken up into water and extracted with ether. The ether phase is washed with water, after which 100 parts of 20% HCl solution are added thereto with vigorous stirring, upon which crystals are formed.

The crystals are filtered, washed with water and then with ether, after which they are dried, to give 21.5 parts 1-[(2,3-dihydro-4H-1,4-benzodioxin)-2-ylmethyl]-4-(4-methyl-α-ethylene-dioxybenzyl)piperidine hydrochloride, M.p.=225° C.

21.5 parts of this compound are then heated to the boiling temperature for 2.5 hours, with 120 parts isopropanol, 30 parts H$_2$O and 60 parts concentrated HCl.

After evaporation to dryness, the residue is taken up into water, neutralized with NaOH and extracted with ethyl acetate, to give 19 parts 1-[(2,3-dihydro-4H-1,4-benzodioxin)-2-ylmethyl]-4-(4-methylbenzoyl)piperidine as white crystals. M.p.(inst.)=114° C.

The latter compound is converted to the hydrochloride, by reaction with HCl within isopropanol. White crystals. M.p.=250° C.

EXAMPLE 11

1-[(2,3-Dihydro-4H-1,4-benzodioxin)-2-ylmethyl]-4-(4-ethylbenzoyl)piperidine hydrochloride In a reactor provided with a stirring device, a mixture of 27 parts 4-(4-ethyl-α-ethylene-dioxybenzyl)piperidine, 24.5 parts 2-hydroxymethyl-2,3-dihydro-4H-1,4-benzodioxine methanesulfonate, 14 parts potassium carbonate and 300 parts dimethylformamide is heated to 100° C. for 24 hours.

When the reaction is complete, DMF is removed under reduced pressure, the residue is taken up into water and extracted with ether.

100 Parts 20% HCl solution are then added to the ethereal solution, with stirring, upon which 1-[(2,3-dihydro-4H-1,4-benzodioxin)-2-ylmethyl]-4-(4-ethyl-α-ethylenedioxybenzyl)piperidine hydrochloride crystallizes out. The compound is obtained in a yield of 26 parts. M.p.=250° C.

22 Parts of this compound are then heated to the boiling temperature for 2.5 hours, with 120 parts isopropanol, 30 parts H$_2$O and 60 parts concentrated HCl.

The resulting material is evaporated to dryness, taken up into water, neutralized, and extracted with ethyl acetate, to give, after the usual treatment, 19.3 parts 1-[(2,3-dihydro-4H-1,4-benzodioxin)-2-ylmethyl]-4-(4-ethylbenzoyl)piperidine, as an oil.

This oil is converted to the hydrochloride by reaction with HCl within isopropanol. White crystals. M.p.=205° C.

EXAMPLE XII

1-[(2,3-dihydro [4H] 1,4-benzodioxin)2-yl] ethyl 4-(4-fluorobenzoyl) piperidine and its hydrochloride.

Step A

Methyl 2-[(2,3-dihydro [4H] 1,4-benzodioxin)-2 yl] acetate 125 g 2-cyanomethyl 2,3-dihydro [4H] benzodioxin (obtained according to the process disclosed in the U.S. Pat. No. 3,149,108), 250 ml water, 250 g acetic acid and 100 g sulphuric acid are mixed together and heated to reflux for 48 hours. The whole mixture is let to revert to room temperature and then poured in cold water. The resulting suspension is thereafter extracted three times with ether. The ethereous solutions are united then extracted with sodium hydroxide solutions. The aqueous phase is thereafter made acidic by adding enough hydrochloric acid. The aqueous solution is further extracted with ether. The ether solutions are washed with water, dried, concentrated to dryness. 197 g of the raw acetic acid derivative are recovered.

174 g of the raw acetic acid derivative are suspended in 2000 g methanol and 20 g p toluene sulphonic acid. The mixture is heated to reflux for 20 hours, then the solvent is evaporated off. The oily residue is taken up in water and extracted with ether. The organic solution is washed with dilute sodium hydroxide solution, with water then dried and distilled to dryness. 168 g of crude methyl ester are thus obtained which is further purified by fractional distillation. The pure compounds boils at 121°-125°/0.5 mm Hg. The yield amounts to 160 g.

Step B 2-(2-hydroxyethyl) (2,3-dihydro [4H] 1,4-benzodioxin)

In a three-neck flask fitted with a mechanical stirring device, 60 g lithium aluminium hydride are suspended in 1300 ml ether. A solution of 160 g methyl 2-[(2,3-dihydro [4H] 1,4-benzodioxin)-2 yl] acetate in 1220 ml ether is cautiously added thereto while keeping the temperature beneath 20°. When the addition is achieved, the reaction mixture is heated to reflux for 18 hours. The mixture is thereafter cooled and the excess of reagent is destroyed.

The solution is filtered and the filtrate is distilled off. The oily residue is further purified producing 126 g of 2-(2-hydroxyethyl) (2,3-dihydro [4H] 1,4-benzodioxin) which boils at 135-140/1 mm Hg.

Step C 2-(2-p toluenesulfonyloxy ethyl) (2,3-dihydro [4H] 1,4-benzodioxin)

74 g of 2-(2-hydroxyethyl) (2,3-dihydro [4H] 1,4-benzodioxin) are dissolved in 150 ml pyridine and to this solution 76 g p toluene sulfochloride are added while maintaining the inner temperature beneath 25°. The whole mixture is kept under stirring at room temperature for 24 hours then poured in water and extracted with chloroform. The chloroformic solutions are united, washed with water, dried and evaporated off. The dry residue is further purified by recrystallizing it from a mixture isopropyl ether—petrol (50:50)

33 g of the p toluene sulfonyl ester are thus produced Melting point 95°.

Step D

1-[(2,3-dihydro [4H] 1,4-benzodioxin-2) yl] ethyl 4-(4-fluoro$\alpha\alpha$-ethylenedioxy benzyl) piperidine.

A mixture of 33 g of 2-(2- p toluenesulfonyloxy ethyl) (2,3-dihydro [4H] 1,4-benzodioxin), 28 g potassium carbonate, 30.4 g (4-fluoro$\alpha\alpha$-ethylenedioxy benzyl) piperidine as the acetate and 300 ml toluene are heated to reflux for 18 hours. After having the mixture let to revert to room temperature, it is filtered, made acidic with 120 ml 20% solution of hydrochloric acid. The precipitate thus appeared is separated, and heated to reflux with 150 ml isopropanol, 37 ml water and 75 g hydrochloric acid for 2.30 hours. The mixture is thereafter evaporated off, taken up with water, made alkaline with sodium hydroxide and extracted with ethyl acetate. The organic solution is washed with water, dried and evaporated to dryness. 32 g of an oily residue are recovered which substantially consist of 1-(2,3-dihydro [4H] benzodioxin-2-yl) ethyl 4-(4-fluoro$\alpha\alpha$-ethylenedioxy benzyl) piperidine which is used without further purification for the next step of the synthesis.

Step E

The raw 1-[(2,3-dihydro [4H] 1,4-benzodioxin-2 yl)] ethyl 4-(4-fluoro$\alpha\alpha$-ethylenedioxybenzyl) piperidine is dissolved in 150 ml hot isopropanol and to this solution 40 ml of a saturated solution of hydrochloric acid in ether are added. The crystallisation is initiated by scratching and after 12 hours standing in a cool place, the crystals are succion-filtered and dried. They are further recrystallized from isopropanol. 26 g of pure 1-[(2,3-dihydro [4H] 1,4 benzodioxin-2 yl)] ethyl 4-(4-fluoro benzoyl) piperidine are obtained which melts at 225°.

EXAMPLE XIII

1-[(2,3-dihydro [4H] 1,4-benzodioxin-2 yl)]propyl 4-(4-fluoro benzoyl) piperidine and its hydrochloride

Step A 2-(2-bromoethyl) (2,3-dihydro [4H] 1,4-benzodioxin)

In a flask fitted with a stirring device, 126 g of 2-(2-hydroxy ethyl) (2,3-dihydro [4H] 1,4-benzodioxin) obtained according to the process of example XII and 29 g phosphorus tribromide are added while maintaining the inner temperature under 30°. The mixture is thereafter heated at 100° for 3 hours. The reaction mixture is then poured in water and the suspension is extracted with chloroform. The chloroformic solutions are separated, washed with dilute sodium hydroxide solutions then with water, dried and evaporated off. 162 g of an oily residue is recovered then further purified by fractional distillation under reduced pressure. 154 g of the pure bromo derivative are thus obtained which boils at 110°-115°/0.2 mm Hg.

Step B 2-(2-cyanoethyl) (2,3-dihydro [4H] 1,4-benzodioxin)

154 g of the bromo derivative of step A are dissolved in 500 ml ethanol at 70%. 82.5 g potassium cyanide are cautiously added and the whole mixture is heated to reflux while stirring for 20 hours. The mixture is let to revert to room temperature, concentrated to dryness, taken up in water and extracted with ether. The ethereous phases are united, washed with water, dried and evaporated off. 98 g of an oily residue are recovered which are purified by fractional distillation. 81 g of the pure cyanoethyl derivative are obtained, boiling at 155°-160°/2 mm Hg.

Step C

Methyl 3-(2,3-dihydro [4H] 1,4-benzodioxin-2 yl) propionate 72 g 2-(2-cyanoethyl) (2,3-dihydro [4H] 1,4-benzodioxin) are suspended in 100 ml acetic acid, 100 ml water and 40 g sulphuric acid. The whole is heated to reflux for 48 hours and the mixture is thereafter poured in water. The aqueous phase is extracted with ether. The ethereous solution is separated, washed, dried and concentrated off. 76 g of 3-(2,3-dihydro [4H] 1,4-benzodioxin-2 yl) propionic acid are obtained, melting at 102°. This acid is esterified with methanol and p toluene sulphonic acid at the boiling point for 18 hours. After the usual purifications 71 g of the methyl ester are obtained. MP: 55°.

Step D 2-(3-hydroxy propyl) (2,3-dihydro [4H] 1,4-benzodioxin)

Using the same procedure as in example XII step B and starting from 70 g of methyl 3-(2,3-dihydro [4H] 1,4-benzodioxin-2 yl) propionate, 63 g of 2-(3-hydroxy propyl) (2,3-dihydro [4H] 1,4-benzodioxin) are recovered as an oily residue.

Step E 2-(3-p toluene sulphonyloxypropyl) (2,3-dihydro [4H] 1,4-benzodioxin)

Using the same procedure as in example XII step C and starting from 63 g of the hydroxy propylated derivative, 60 g of the p toluene sulphonyloxypropyl derivative are obtained as an oil which is not further purified.

Step F

1-[(2,3-dihydro [4H] 1,4-benzodioxin-2 yl) propyl] 4-(4-fluoro$\alpha\alpha$-ethylenedioxy benzyl) piperidine Using the same procedure as in example XII step D and starting from 35 g of the p toluene sulphonyloxypropyl derivative of Step E, an oily product is recovered which is purified by chromatography on a column of silica and elution with the mixture toluene-isopropylamine (95:5). The ethylene ketal is obtained as a viscous liquid (yield=20 g).

Step G

1-[(2,3-dihydro [4H] 1,4-benzodioxin-2 yl) propyl] 4-(4-fluoro benzoyl) piperidine Using the same procedure as in example XII step E and starting from 20 g of the ethylene ketal of step F, 15 g of 1-[(2,3-dihydro [4H] 1,4-benzodioxin-2 yl) propyl]

4-(4-fluoro benzoyl) piperidine are obtained which melts at 350°–355°. The free base is dissolved in 75 ml hot isopropanol and added to 30 ml 3 N solution of hydrochloric acid in ether. The hydrochloride precipitates, the crystals are separated, washed with isopropanol and dried. 11 g of 1-[(2,3-dihydro [4H] 1,4-benzodioxin-2 yl) propyl] 4-fluoro benzoyl piperidine, hydrochloride are obtained. It melts at 178° C.

EXAMPLE XIV

1-[(2,3-dihydro [4H] 1,4-benzodioxin-2 yl) (1-hydroxy ethyl)] 4-(4-fluoro benzoyl) piperidine

Step A 2-bromacetyl 2,3-dihydro [4H] 1,4-benzodioxin

In a flask 34 g 2-acetyl 2,3-dihydro [4H] 1,4-benzodioxin are dissolved in 1000 ml ether. The mixture is cooled to −10° and 30 g bromine are dropwise added thereto. After 2 hours contact the reaction mixture is washed with a solution of sodium bicarbonate then dried. The solvent is evaporated off, providing an oily residue which is crystallized from petroleum ether. 37 g of the brominated ketone are obtained which melts at 80° C.

Step B 2-(1-hydroxy 2-bromoethyl) (2,3-dihydro [4H] 1,4-benzodioxin)

34 g of 2-(2-bromacetyl) (2,3-dihydro [4H] 1,4-benzodioxin) are dissolved in 350 ml methanol. This solution is cooled to −10° then dropwise added to 10 g sodium borohydride. Once the addition achieved the reaction mixture is kept under stirring for 18 hours at ambient temperature, then evaporated off. The dry residue is taken up in water and extracted with ether. The distillation of the solvent gives rise to the isolation of 28 g of the 1-hydroxy 2-bromoethyl derivative as an oily product.

Step C

1-[(2,3-dihydro [4H] 1,4-benzodioxin)2-yl (1-hydroxy ethyl)]4-[(4-fluoro$\alpha\alpha$-ethylenedioxy benzyl] piperidine A mixture of 26 g of 2-(1-hydroxy 2-bromoethyl) 2,3-dihydro [4H] 1,4-benzodioxin, 30 g of 4-[(4-fluoro$\alpha\alpha$-ethylenedioxy) benzyl] piperidine as the acetate and 28 g potassium carbonate are heated together in 300 ml toluene for 18 hours.

The mixture is thereafter filtered and the filtrate is evaporated to dryness. The residue is taken up in isopropyl ether from which it crystallizes. After filtration 28 g of 1-[2,3-dihydro [4H] 1,4-benzodioxin)2 yl (1-hydroxy ethyl)] 4-[(4-fluoro$\alpha\alpha$-ethylenedioxy) benzyl] piperidine are obtained, melting at 96°.

Step D

1-[(2,3-dihydro [4H] 1,4-benzodioxin)2-yl (1-hydroxy ethyl)] 4-(4-fluoro benzoyl) piperidine The cetal of step C is suspended in 80 ml isopropanol and boiled for 2.30 hours with 20 ml water and 40 ml concentrated hydrochloric acid. After boiling the solvent is evaporated off and the residue is extracted with ethyl acetate. The organic solution is purified by chromatography on a column filled with silica H and elution with a mixture of toluene-isopropylamine (95:5). 10 g of the free ketone are obtained, melting at 130°.

EXAMPLE XV 4-(4-fluoro benzoyl) 1-[(6-methyl 2,3-dihydro [4H] 1,4-benzodioxin-2 yl) methyl] piperidine and its hydrochloride.

Step A 2-hydroxymethyl 6-methyl 2,3-dihydro [4H] 1,4-benzodioxin

In a reactor fitted with a stirring device 149 g 4-methyl pyrocatechol and 144 g epichlorhydrin are mixed together and heated at 70°, then a solution of 53 g sodium hydroxide in 440 ml water is slowly added. The reaction mixture is further heated at 70° for 2.30 hours then poured in water and extracted with ethyl acetate. The resulting raw product is separated after evaporation of the solvent and purified by fractional distillation under reduced pressure. 84 g of the title compound are obtained, boiling at 136°–140°/2 mm Hg.

Step B 2-(p toluene sulphonyloxymethyl) 6-methyl 2,3-dihydro [4H] 1,4-benzodioxin Starting from 72 g of the 2-hydroxymethylated derivative of step A, 76 g p toluene sulphochloride and 150 g pyridine, 84 g of the p toluene sulphonyloxymethylated derivative are obtained which melts at 84°.

Step C

1-[(6-methyl 2,3-dihydro [4H] 1,4-benzodioxin-2 yl)methyl] 4-[(4-fluoro$\alpha\alpha$-ethylenedioxy) benzyl] piperidine Using the same procedure as in example XII step D and starting from 33.5 g of the p toluene sulphonyloxymethylated derivative of step B, 31 g of 4-[(4-fluoro$\alpha\alpha$-ethylenedioxy benzyl] piperidine as the acetate and 28 g potassium carbonate, 33 g of 1-[(6-methyl 2,3-dihydro [4H] 1,4-benzodioxin-2 yl) methyl] 4-[(4-fluoro$\alpha\alpha$-ethylenedioxy) benzyl] piperidine are obtained which melts at 250°.

Step D

1-[(6-methyl) 2,3-dihydro [4H] 1,4-benzodioxin-2 yl) methyl] 4-(4-fluoro benzoyl) piperidine and its hydrochloride.

33 g of the ethylene ketal of step C are boiled together with 110 ml isopropanol, 30 ml water and 60 g concentrated hydrochloric acid for 2.30 hours. After evaporation of the solvent to dryness, the dry residue is taken up in water, made basic by adding enough sodium hydroxide and extracted with ethyl acetate. After distillation of the solvent 30 g of an oily residue are recovered.

The free base is converted into its hydrochloride by dissolving it in isopropanol and adding to the solution a 3 N solution of hydrochloric acid in ether. The hydrochloride is isolated by succion-filtration, washed and dried. 23 g of the hydrochloride are obtained melting at 200°.

EXAMPLE XVI

1[(7-methoxy 2,3-dihydro [4H] 1,4-benzodioxin 2-yl)methyl] 4-(4-fluoro benzoyl) piperidine and its hydrochloride.

Step A 2-chloromethyl 2,3-dihydro [4H] 1,4-benzodioxin

In a three neck flask fitted with a stirring device, 218 g thionyl chloride are mixed with 1000 g pyridine while cooling. They are added further, portionwise 500 g 2(hydroxy methyl) (2,3-dihydro [4H] 1,4-benzodioxin) while keeping the inner temperature below 20°. When the reaction is completed, the mixture is heated at 100° for 3 hours then poured into water and extracted with chloroform. The solvent is distilled off and the raw residue is purified by fractional distillation under reduced pressure. 340 g of the chloromethylated derivative are obtained. It boils at 85°–90°/0.2 mm Hg.

Step B 2-chloromethyl 7-nitro 2,3-dihydro [4H] 1,4-benzodioxin 92 g of 2-chloromethyl 2,3-dihydro [4H] 1,4-benzodioxin are dissolved in 675 ml acetic acid. In this solution it is added a mixture of 500 ml acetic acid and 250 ml nitric acid while keeping the temperature below 20°. The mixture is kept at room temperature for 2 hours then heated at 90° for 1 hour. It is thereafter poured in water and extracted with methylene chloride. 102 g of the nitroderivative are obtained. It is in the form of yellow crystalls which melt at 60°–62°.

Step C 2-chloromethyl 7-amino 2,3-dihydro [4H] 1,4-benzodioxin 150 g of 2-chloromethyl 7-nitro 2,3-dihydro [4H] 1,4-benzodioxin are dissolved in 2600 ml ethanol. 15 g of palladium on coal are added and the whole mixture is hydrogenated at room temperature and atmospheric pressure.

After filtration of the catalyst and evaporation of the solvent, 130 g of an oily product are obtained. For the sake of purification it is converted into its hydrochloride by adding a solution of hydrochloric acid in ether. 110 g of hydrochloride are obtained. Melting point 210°.

Step D 2-chloromethyl 7-hydroxy 2,3-dihydro [4H] 1,4-benzodioxin 24 g of the amino derivative of step C as the hydrochloride are dissolved in 500 ml water. 20 ml concentrated hydrochloric acid are added then dropwise a solution of 9 g sodium nitrite in 10 ml water. The resulting solution is kept aside in a cool place, then dropwise added to a solution of 100 g sulphuric acid in 75 ml water previously heated to 100°. The whole mixture is poured in water and extracted with ether. The ethereous phase is separated and extracted with a 10% solution of sodium hydroxide. The aqueous phase is recovered, made acidic and extracted with ethyl acetate. The solvent is distilled off and an oily residue is obtained which is distilled under reduced pressure. 10 g of 2-chloromethyl 7-hydroxy 2,3-dihydro [4H] 1,4-benzodioxin are thus produced. It boils at 143°–145°/0.2 mm Hg.

Step E 2-chloromethyl 7-methoxy 2,3-dihydro [4H] 1,4-benzodioxin 20 g of the 7-hydroxy derivative of step D are dissolved in 400 ml acetone and 80 g potassium carbonate are added to this solution. 30 g of methyl sulphate are slowly added and heated thereafter at the reflux for 20 hours.

After this set of time the mixture is filtered, the filtrate is evaporated to dryness. The dry residue is taken up in ether, washed with an aqueous solution of sodium bicarbonate then with water. The organic solution is dried on sodium sulphate and evaporated off. The residue is further purified by fractional distillation under reduced pressure. 14 g of 2-chloromethyl 7-methoxy 2,3-dihydro [4H] 1,4-benzodioxin are obtained. It boils at 114°–118/0.2 mm Hg.

Step F 36 g of 2-chloromethyl 7-methoxy 2,3-dihydro [4H] 1,4-benzodioxin, 42 g 4-[(4-fluoro$\alpha\alpha$-ethylenedioxy) benzyl] piperidine and 23 g potassium carbonate are suspended into 400 ml dimethyl formamide. The whole mixture is heated at 100° for 18 hours then concentrated to dryness under reduced pressure. The residue is taken up in water and the aqueous phase is extracted with ether. To the ethereous solution 160 ml 20% hydrochloric acid solution are added and the crystalline hydrochloride of 1-[(7-methoxy 2,3-dihydro [4H] 1,4-benzodioxin)-2 yl methyl] 4-[(4-fluoro$\alpha\alpha$-ethylenedioxy) benzyl] piperidine precipitates. The hydrochloride is separated by filtration, washed with ether and dried. 33 g of the hydrochloride are thus obtained. Its melting point is 230°.

Step G

1-[(7-methoxy 2,3-dihydro [4H] 1,4-benzodioxin)-2 yl methyl] 4-(4-fluoro benzoyl) piperidine and its hydrochloride 33 g of the hydrochloride of step F are dissolved in 160 ml isopropanol and 40 ml water. 80 ml concentrated hydrochloride are added and the reaction mixture is heated to reflux for 2.30 hours. The solvents are thereafter distilled off and the residue is taken up in water then extracted with ethyl acetate from which the desired piperidine crystallises. This compound is further purified by recrystallisation from isopropyl ether 13 g of 1-[(7-methoxy 2,3-dihydro [4H] 1,4-benzodioxin)2-yl methyl] 4-(4-fluoro benzoyl) piperidine are obtained. Melting point 105°.

The free base is converted into its hydrochloride (yield=11 g) which melts at 180°.

EXAMPLE XVII

1-[(2,3-dihydro [4H] 1,4-benzodioxin)2-yl methyl] 4-(4-fluoro$\alpha$hydroxybenzyl) piperidine and its hydrochloride 20 g of 1-[(2,3-dihydro [4H] 1,4-benzodioxin)2-yl methyl] 4-(4-fluoro benzoyl) piperidine obtained according to the procedure of example I are dissolved in 800 ml methanol. To this solution 4.6 g sodium borohydride are slowly added while keeping the temperature of the mixture below 25°. After one hour contact, the solvent is evaporated off and the residue is taken up in water then extracted with ethyl acetate. The solvent is thereafter distilled and the oily residue consisting of 1-[(2,3-dihydro [4H] 1,4-benzodioxin)-2yl methyl] 4-(4-fluoroα-hydroxy benzyl) piperidine is dissolved in 500 ml ether to which 40 ml of 3 N solution of hydrochloric acid in ether is added.

The hydrochloride crystallizes soon, is separated by filtration, washed and dried. It is further recrystallized from acetonitrile.

7 g of the hydrochloride are obtained. Melting point 140°–142°.

EXAMPLE XVIII

1-[(2,3-dihydro [4H] 1,4-benzodioxin)-2 yl methyl] 4-(4-fluoroα-methylα-hydroxy benzyl) piperidine and its hydrochloride A fresh solution of methyl magnesium iodide is prepared by reacting 1.8 g magnesium turnings with 10.7 g methyl iodide in 50 ml ether. When the reaction is complete, a solution of 18 g of 1-[(2,3-dihydro [4H] 1,4-benzodioxin)2-yl methyl] 4-(4-fluoro benzoyl) piperidine of example I in 75 ml tetrahydrofuran is slowly added. After completion of the addition the reaction mixture is heated for 3 hours to the reflux.

The excess of reagent is destroyed by adding a solution of magnesium chloride. The reaction mixture is thereafter extracted with ethyl acetate. The solvent is evaporated off and 20.5 g of an oily product are recovered.

This oily base is converted into its hydrochloride with a solution of hydrochloric acid in ether. The hydrochloride is recrystallized from acetonitrile. 9 g of the pure hydrochloride are obtained. Melting point 245°.

EXAMPLE XIX

Pharmacological testing of the compounds of formula I

Results of pharmacological and toxicological testing of the compounds of formula I are given below. Said results are given predominantly for the compound of Example 2 which is the most representative compound of this genus.

I Cardiovascular properties (a) Effect on the blood pressure of anesthetized normotensive animals The investigation was carried out on three species (rats, rabbits and dogs). The compound to be tested was administered intravenously. The different parameters recorded were the systolic, diastolic and mean blood pressures, the heart rate, the systolic ejection rate (dp/dt).

The cardiac contraction force, the arterial and venous rates of flow were recorded only in dogs.

At low dosage the compounds induce an instant systodiastolic pressure drop, which is proportional to the dosages both as to intensity and as to duration, together with brachycardia in rats. In dogs, an increase of the cardiac contraction force, an increase of the dp/dt and an increase of the arterial and venous rates of flow was found to occur concomitantly with hypotension.

Thus, under the above experimental conditions, the compounds appear to be powerful hypotensive agents which do not induce any depression in the cardiac performances.

(b) Effect on the blood pressure of non-anesthetized hypertensive animals

The investigation was conducted in rats and dogs. Use was made, on the one part, of animals (rats) rendered hypertensive by ligation of the abdominal aorta between both renal arteries and, on the other part, of animals (rats strain Okamoto and dogs) which exhibited a spontaneous hypertension.

The compound to be tested was administered orally, either as a single dose to evidence the kinetics of the action of the product, or for an extended treatment period.

In experimental models, it exhibits a marked extended anti-hypertensive action, which increases with the dosages up to a maximum value. In dogs, a persistence of the anti-hypertensive effect after interruption of the treatment, with gradual return to normal, may be noted.

The figures obtained with the compound of Example 2 in rats and dogs are set forth in Tables I and II

TABLE I

| Dose mg/kg P.O. | Blood pressure drop (mm Hg) in rats | | | | | | | |
|---|---|---|---|---|---|---|---|---|
| | 10 mn | 30 mn | 1 hr | 2 hrs | 6 hrs | 12 hrs | 18 hrs | 24 hrs |
| 10 | 39 ± 11 | 45 ± 10 | 33 ± 9 | 20 ± 6 | 6 ± 3 | — | — | — |
| 20 | 66 ± 8 | 63 ± 6 | 49 ± 7 | 37 ± 7 | 29 ± 6 | 17 ± 7 | 8 ± 4 | 3 ± 3 |
| 50 | 68 ± 6 | 68 ± 3 | 52 ± 6 | 38 ± 7 | 32 ± 8 | 16 ± 7 | 8 ± 5 | 5 ± 5 |

TABLE II

| Dose mg/kg P.O. | Blood pressure drop (mm Hg) in dogs | | | | | | |
|---|---|---|---|---|---|---|---|
| | 20 mn | 40 mn | 1 hr | 2 hrs | 5 hrs | 7 hrs | 24 hrs |
| 10 | 10 ± 4 | 10 ± 4 | 18 ± 3 | 11 ± 1 | 4 ± 3 | 1 ± 2 | 0 ± 1 |
| 20 | 12 ± 4 | 26 ± 3 | 38 ± 2 | 37 ± 3 | 18 ± 7 | 8 ± 1 | 2 ± 3 |
| 50 | 21 ± 9 | 31 ± 6 | 40 ± 8 | 46 ± 3 | 28 ± 8 | 22 ± 6 | 1 ± 2 |

II Effects on the central nervous system

In mice, it was found that oral administration of the compound of Example 2 produces a state of sedation, a decrease of the aggressiveness, and a potentiation of the experimentally-induced sleep at the same dosages which induce an anti-hypertensive activity in rats. Such central effects may be directly related to the hypotensive action.

III Toxicity (a) Acute toxicity

Toxicity was determined in mice by the oral route. The results obtained are set forth in Table III.

TABLE III

| Example | Approximate lethal dose 50 (LD$_{50}$), mg/kg, per os |
|---|---|
| 2 | 495–655 |
| 4 | 364 |
| 6 | 880 |
| 7 | 440 |
| 8 | >3200 |
| 9 | 2400 |
| 10 | 1460 |

TABLE III-continued

| Example | Approximate lethal dose 50 (LD$_{50}$), mg/kg, per os |
|---|---|
| 11 | 1200 |

(b) Chronic toxicity

The compound to be tested, admixed with food, was administered to rats for 45 days.

At 75 mg/kg/day, it does not induce any hematological or anatomical anomaly. From a biochemical standpoint: a marked, isolated, drop of the triglyceride level is noted.

At 300 mg/kg/day, it has no lethal effects, but induces biochemical and anatomical changes, the more noteworthy of which are a very marked decrease of the triglycerides without modification of the SGOT, and an almost complete lysis of the adipose tissues.

At 400 mg/kg/day and above it induces a higher death rate in females than in males.

What we claim is:

1. A compound selected from the group consisting of 1-[(2,3-dihydro {4H} 1,4-benzodioxin) 2-yl] methyl-4-(4-fluoro-α-methyl-α-hydroxy benzyl) piperidine and a therapeutically acceptable acid addition salt thereof.

2. An anti-hypertensive pharmaceutical composition containing as active ingredient an anti-hypertensive effective amount of at least one compound of claim 1 in admixture or conjunction with an inert non-toxic pharmaceutically-acceptable carrier or vehicle.

3. A pharmaceutical composition of claim 2 wherein the amount of active ingredient ranges from 10 to 200 mg per unit dosage.

4. A method for treating hypertension in hypertensive mammals which comprises administering to said patients suffering from hypertension a safe but effective amount of a compound of claim 1.

5. The method of claim 4 wherein the safe but effective amount of a compound of claim 1 ranges from 20 to 400 mg daily in man.

* * * * *